United States Patent [19]

Hsu et al.

[11] Patent Number: 5,158,887
[45] Date of Patent: Oct. 27, 1992

[54] PROCESS FOR MASSIVE CONVERSION OF CLOSTRIDIA IN SYNCHRONIZED CELLS OF ELONGATED LENGTH OR REFRACTILE ENDOSPORES

[76] Inventors: Edward J. Hsu, 50 E. Concord, Kansas City, Mo. 64112; Sandra L. Landuyt, 511 N. Forrest Ave., Liberty, Mo. 64068

[21] Appl. No.: 707,177
[22] Filed: May 24, 1991

Related U.S. Application Data

[63] Continuation-in-part of Ser. No. 565,047, Sep. 9, 1990, abandoned.
[51] Int. Cl.[5] ............................................. C12N 1/20
[52] U.S. Cl. .................................. 435/252.7; 435/136; 435/140; 435/141; 435/160; 435/161; 435/162; 435/163; 435/252; 435/277; 435/813; 435/842
[58] Field of Search ...................... 435/252.7, 136, 140, 435/141, 160, 176, 277, 161, 162, 163, 252, 813, 842

[56] References Cited

U.S. PATENT DOCUMENTS

| | | | |
|---|---|---|---|
| 4,292,406 | 9/1981 | Ljungdahl et al. | 435/42 |
| 4,349,628 | 9/1982 | English et al. | 435/161 |
| 4,652,526 | 3/1987 | Hsu | 435/253 |
| 4,778,760 | 10/1988 | Ishida | 435/202 |

OTHER PUBLICATIONS

Hoffmann in Chambliss et al. (Ed) Spores VII Intl Spore Conf. Madison, WI Oct. 5-8, 1977 ASM (Wash. DC) 1978 pp. 312-318.
Hsu In: Spore Research (ed G. W. Gould et al) pp. 223-242 Academic Press, London 1976.
Applied Microbiology & Biotechnology; 1986 (23:369-371).
Transition from Acid Fermentation to Solvent Fermentation in a Continuous Dilution Culture of *Clostridium Thermosaccharolyticum*, Landuyt, Hsu–pp. 473–478.
Solvent Fermentation Precedes Acid Fermentation in Elongated Cells of *Clostridium Thermosaccharolyticum*, Landuyt and Hsu, 1985, pp. 485–501.
Interruption in Cell Division by Catabolite Dilution Producing Synchronous Growth of *Clostridium Thermosaccharolyticum;* Hoffman, Chang & Hsu, pp. 312-318.
Synchronous Elongation of *Clostridium Thermosaccharolyticum* and its Relation to Stage I of Sporulation; Hsu; pp. 223-242.
Comparative Metabolism of Vegetative and Sporulating Cultures of *Clostridium Thermosaccharolyticum;* Hsu and Ordal; Feb. 9, 1970; Journal of Bacteriology, pp. 369-376.
Sporulation of *Clostridium Thermosaccharolyticum* Under Conditions of Restricted Growth; Journal of Bacteriology, Mar. 1969, pp. 1511-1512.
Sporulation of *Clostridium Thermosaccharolyticum;* Applied Microbiology, Nov. 1969, pp. 958-960.

*Primary Examiner*—Douglas W. Robinson
*Assistant Examiner*—Jane A. Williams
*Attorney, Agent, or Firm*—Hovey, Williams, Timmons & Collins

[57] ABSTRACT

A method is disclosed for producing specially prepared bacteria of the genus Clostridium for producing solvents, enzymes, antibiotics, toxic proteins, or spores. Cell elongation to a critical length of at least about 3x is induced in an economical, abundantly available growth medium by serial subculturing under controlled conditions to effect synchronization of growth in the number of the cells and their effective mass and to produce a substantially homogeneous cell population. At least about 0.01M of a divalent cation such as calcium is added to the synchronized cells of critical length to stabilize the cells against death, lysis or aggregation. Where bacterial production of solvents is desired, cell division is inhibited by temperature shift or by chemical means when the cells reach a synchronized solventogenic state. Solvents produced by the specially prepared bacteria may be economically and readily recovered by conventional distillation procedures or the like. If the specially prepared bacteria are to be used for production of products other than solvents, growth of the synchronized, stabilized cells is inhibited by temperature shift and the cells are allowed to differentiate and continue metabolism and sporulation until the resultant bacteria are useful for preferential production of the desired enzymes, antibiotics or toxic proteins. Spore formation may be permitted to continue until substantially the entire cell population constitutes refractile mature free spores, which may be harvested and stored for future use.

22 Claims, 5 Drawing Sheets

FIG. 5

PROCESS FOR MASSIVE CONVERSION OF CLOSTRIDIA IN SYNCHRONIZED CELLS OF ELONGATED LENGTH OR REFRACTILE ENDOSPORES

This application is a continuation-in-part of application Ser. No. 07/565,047, filed Sep. 9, 1990, now abandoned.

BACKGROUND OF THE INVENTION

1. Field of the Invention

The present invention relates to a method for synchronizing the growth of clostridia useful in the production of solventogenic cells, enzymes, antibiotics, useful toxic proteins, or refractile endospores. Vegetative cells of bacteria of the genus Clostridium may be massively converted to synchronized solventogenic cells of essentially the same critical length, or the conversion allowed to proceed in a manner such that the production of refractile endospores is selectively induced. More particularly, the bacteria are synchronized in cell number and mass by selective subculturing in a medium containing a slowly metabolizable carbon source to avoid random cell growth. The synchronized cells are elongated to at least three times the length of vegetative cells, at which point they become solventogenic. Synchrony of cell mass and number is stabilized by addition of at least about 0.01M of a divalent cation to the medium. If solventogenesis is to be preserved, growth must be inhibited by chemical or physical means. Where preparation of enzymes, antibiotics or toxic protein producing cells is desired, cell growth may be arrested at selected growth stages beyond the solventogenic stage by inhibition of cell division or DNA replication.

2. Description of the Prior Art

Some anaerobic, thermophilic, endospore-forming bacteria of the genus Clostridium are capable of only limited metabolic production of enzymes, antibiotics, toxic proteins, or for producing solvents by acetone-butanol-ethanol (ABE) fermentation. The special capabilities of this genus are largely attributable to their expanded genetic versatility, where significant production of endospores occurs only under a particular physiological condition. Endospores are characterized by their ability to withstand extreme conditions which would destroy the cells in their vegetative state. The morphological changes exhibited by clostridial cells are related to changes in cellular enzyme activity. Depending upon the culture conditions, these bacteria can enter either an acidogenic phase or a solventogenic phase in the process of growth. Regulation of the overall sporulation process is thus a necessary prerequisite to the commercial production of cellular metabolites.

Some species of bacteria of the genus Clostridium are directly capable of converting low cost biomass wastes, such as xylan, or other pentose polymers, into solvents without prior depolymerization of the substrate. By virtue of the fact that certain clostridia are anaerobic and thermophilic, industrial fermentation processes using this genus may be carried out at relatively high temperatures. As a consequence, recovery of their fermentation products requires less energy because it can be accomplished by vacuum distillation directly from the fermentation vessel. Vacuum recovery also reduces the problems associated with solvent toxicity to the fermenting cells. The clostridia have high metabolic rates thus reducing the required residence time in the bioreactor and the ratio of end products to cells is high, maximizing the total bioreactive output. In addition, the use of a thermophilic system along with a simplified culture medium and defined and massive numbers of inoculated cells, assures that the system is inherently less subject to contamination. Sterilization of the raw materials therefore may be eliminated.

Lignocellulosic biomass material, the cheapest and most abundant feedstock for bacterial fermentation processes, has three major fractions: crystalline cellulose, hemicellulose, and lignin, each of which must be separately processed. Cellulose can be hydrolyzed to glucose with acid or enzyme catalysts. However, acid catalyst continue to degrade the resulting glucose. Furthermore, enzyme processes are not yet well developed and consequently are not cost efficient. Hemicellulose is largely composed of xylan, which is easily hydrolyzed to xylose but difficult to ferment to ethanol with existing fermentation technologies. Lignin is not a sugar polymer and, therefore, cannot be fermented to produce ethanol but can be thermochemically converted for use as a liquid fuel additive.

Use of anaerobic *Clostridium acetobutylicum* for industrial solvent production began at least as early as the 1920's employing a cane molasses feedstock. However, the best solvent yield obtainable was about 1.8% and even this yield was unreliable and unstable due to the susceptibility of *C. acetobutylicum* to phage (bacterial virus) infection. The method of the present invention enables control of the rates and yields of product formation and use of cheaper lignocellulose feedstocks. In especially preferred forms, the present invention utilizes thermophilic organisms of the genus Clostridium which, because of their ability to grow at elevated temperatures, make the process more energy efficient. In addition, thermophilic clostridia are not susceptible to phage infections.

One form of synchronous elongation of *Clostridium thermosaccharolyticum* is described in a chapter by Edward J. Hsu, one of the inventors hereof, in Spore Research, published by Academic Press (London, 1976, pp. 223-242), but that description makes no reference to synchronous growth of the cells in the presence of a divalent cation capable of stabilizing the cells during at least final multiplication thereof.

Ethanol-producing mutants of *Clostridium thermosaccharolyticum* are described in U.S. Pat. No. 4,652,526 issued to Edward J. Hsu, one of the inventors hereof. This patent also makes no mention of synchronous growth of cells in a growth medium under conditions where a divalent cation is added to stabilize the cells.

Hartmanis, et al. in Applied Microbiology and Biotechnology, Vol. 23 (1986) at pp. 369-371 describe repetitious subculturing of *Clostridium acetobutylicum* in a growth medium containing quantities of divalent cations. A small amount of calcium was included in the starter culture to prevent degeneration of the cells after only three transfers. The addition of $CaCO_3$ permitted as much as ten transfers without degeneration. The calcium addition thus eliminated the need for multiple heat shock treatments for the preparation of a starting culture. However, synchronization of growth in the number of cells and their effective mass was not carried out to produce a substantially homogeneous cell population. The authors described a process wherein each subculture was allowed to progress for at least about a 24 hour interval to produce heat resistant spores. It was reported that the minor amount of calcium in the growth medium appeared to render the spores more heat-resistant.

U.S. Pat. No. 4,778,760 to Ishida, et al. indicates that a slight amount of calcium (4 ppm) is useful to stabilize a thermostable α-amylase-producing thermophilic anaerobic bacteria of the Clostridium class. However, the calcium is not utilized as a component of the growth medium for the bacterial cells.

SUMMARY OF THE INVENTION

The present invention allows bacteria of the genus Clostridium to be prepared which are useful for selective production of solvents, such as ethanol and butanol at significantly higher levels than heretofore obtainable. In addition, enzymes or antibiotics may be selectively produced. Of equal importance is the fact that whereas previously solvent recoveries have not exceeded about 1 to 2%, this process permits as much as about 11% of the solvent to be recovered. Butanol and ethanol may be recovered in a ratio of 2:1 at solvent recovery levels of 11%. The ethanol recovery ratio is increased to 1:1 at solvent recovery levels of 6.5%. Advantageously low cost feed stocks may be used as the growth medium for specially prepared cells. Optionally, the process of cell preparation may be allowed to proceed to full spore formation, all of which is accomplished more efficiently than with past practices.

The preferred method hereof broadly includes synchronized growth in the number and mass of substantially anaerobic clostridial cells to a critical length. The cells are grown in batch cultures on a low cost carbon source growth medium. The resultant cells of the synchronized culture are at exactly the same stage in the division cycle and the individual cells and their respective processes are said to be "in phase". Depending on the desired end product, the cells may be harvested and stored or the procedure continued with stabilization of the cells by addition of a divalent cation source, followed by inhibition of cell growth. The resultant bacteria are capable of continued metabolism for extended periods of time. Metabolic end products which may be isolated from such cells include solvents, carbohydrate degrading enzymes, proteases, lipases, nucleases, antibiotics, parasporo-like protein crystals, and other toxic proteins as, for example, those which are useful as organic insecticides.

The preferred growth medium is a species-specific basal medium containing about 0.1 to 15.0% on a weight to volume basis of a slowly metabolized carbon source. The growth rate of the bacteria in such medium should be 10–90% less than the maximum growth rate $K_m$ for the bacteria in their optimum growth medium. Most preferably, the carbon source may be a pentose polymer such as xylan which may be economically obtained from wheat straw, rice straw, rice hulls, cornstalks, corncobs, fruit peels, hemicellulose and cellulosic residues from paper mill waste or other suitable organic agricultural, industrial, or urban waste.

The cells are synchronized by one or more preferred methods of repeated dilution, centrifugation, or membrane filtration, each followed by repeated subculture. The cells are grown at a temperature of from about −20° C. to about +10° C. of the species-specific optimum growth temperature. The growth period is limited to about 1.0 to 1.5 generations, or 1.0 to 1.5 times the "doubling" time, that is, the time required for a culture to multiply two to three times the initial concentration.

At least about three to four discrete growth periods interspersed respectively with two to three dilutions, centrifugations or membrane filtrations to remove cell metabolic wastes are required to synchronize the cells. In preferred embodiments the synchronized cells are all of essentially the same critical length within a range of from at least about 3× and preferably about 4× to about 20× the length of normal vegetative cells. However, the cells may be elongated up to 100× their vegetative length.

The elongated, synchronized cells are subcultured to allow the cells to further multiply from about 1.0 to 12.0 generations, that is, the time required for the culture to multiply 2 to 4,096 times their prior concentration. The cells are subcultured in a growth medium containing a divalent cation such as calcium, magnesium, manganese, iron, or zinc to stabilize the activity of the cells and to prevent their death, lysis or aggregation. Good results are obtained by addition of at least about 0.01M of the divalent cation to the growth medium. A quantity of the divalent cation may be utilized which exceeds the solubility thereof in the growth medium, with the excess of the divalent compound dissolving as the divalent cation is incorporated in the cells undergoing multiplication. Better results are obtained if the divalent cation concentration is maintained at a level of from at least about 0.01M to about 0.2M with the preferred concentration of the divalent cation being at least about 0.1M. Three kinds of media may be used: one in which xylan is the sole carbon source, and the xylan is supplemented with a divalent cation; one in which xylan is supplemented with an additional carbon source that is the divalent salt of an organic acid; and one in which the divalent salt of an organic acid is the sole carbon source. An organic calcium compound such as calcium gluconate, lactate, acetate, butyrate, or formate is preferred. Synchronized cells stabilized with calcium gluconate can be sustained, even in the presence of growth inhibitors, for six months calcium gluconate is the most preferred divalent cation source because it provides not only as the required divalent calcium ion, but also serves as an excellent carbon source which is metabolized in a manner similar to that of glucose but at a much slower rate.

Cultures that are synchronized by sequential transfer (at least two subcultures) in a medium that contains a slowly metabolizable carbon source results in a type of modified cell division not previously reported for any type of bacteria, including the Clostridium species. In accordance with the present invention the cells, for example, elongate 16× to 20×, and form a single septum to divide the cell in an unusual modified manner such that the filament is equally divided into two cells that remain elongated. When septation is observed on the newly formed cells that are 8× to 10× in length, it is either to divide the cell equally once again, or terminally to form a spore septum. Therefore, a cell elongates, for example, to 16×, divides equally to form two cells that are elongated 8× and subsequently divided to form four cells that remain elongated 4× (the critical length).

Suitable sources of a slowly metabolizable carbon source include amygdalin, arabinose, cellobiose, galactose, glycogen, melibiose, α-methylglucoside, β-methylglucoside, raffinose, salicin, starch, trehalose, xylan, Ca-acetate, Ca-butyrate, Ca-citrate, Ca-formate, Ca-gluconate, and Ca-lactate.

Previous attempts to produce a relatively homogeneous population of free, refractile spores of *C. thermosaccharolyticum* have been unsuccessful. The method of the present invention includes culture-conditions that permit the complete differentiation of vegetative cells to such an extent that virtually 100% free refractile spores may be produced.

Where the desired end product is cells to be sold as a commodity, they may be harvested and washed by repeated centrifugation and resuspension or by filtration and stored at 4° C. On the other hand, if the desired end product is spores, the temperature of the stabilized culture is preferably raised or lowered beyond the culture growth range, e.g., $-20°$ C. to about $+10°$ C. of the optimum temperature for growth. Cell division will cease at that temperature, but cell differentiation, spore formation and metabolism will continue. If the desired end product is one that can be produced by elongated, sporulating cells, e.g. solvents, growth of the resulting synchronized, stabilized cells is preferably inhibited by temperature modification, or use of antimicrobial chemical agents such as antibiotics and dyes. Spore formation as well as cell division cease upon such addition but metabolic processes such as solvent production continue.

DESCRIPTION OF THE PREFERRED EMBODIMENTS

Figure 1:
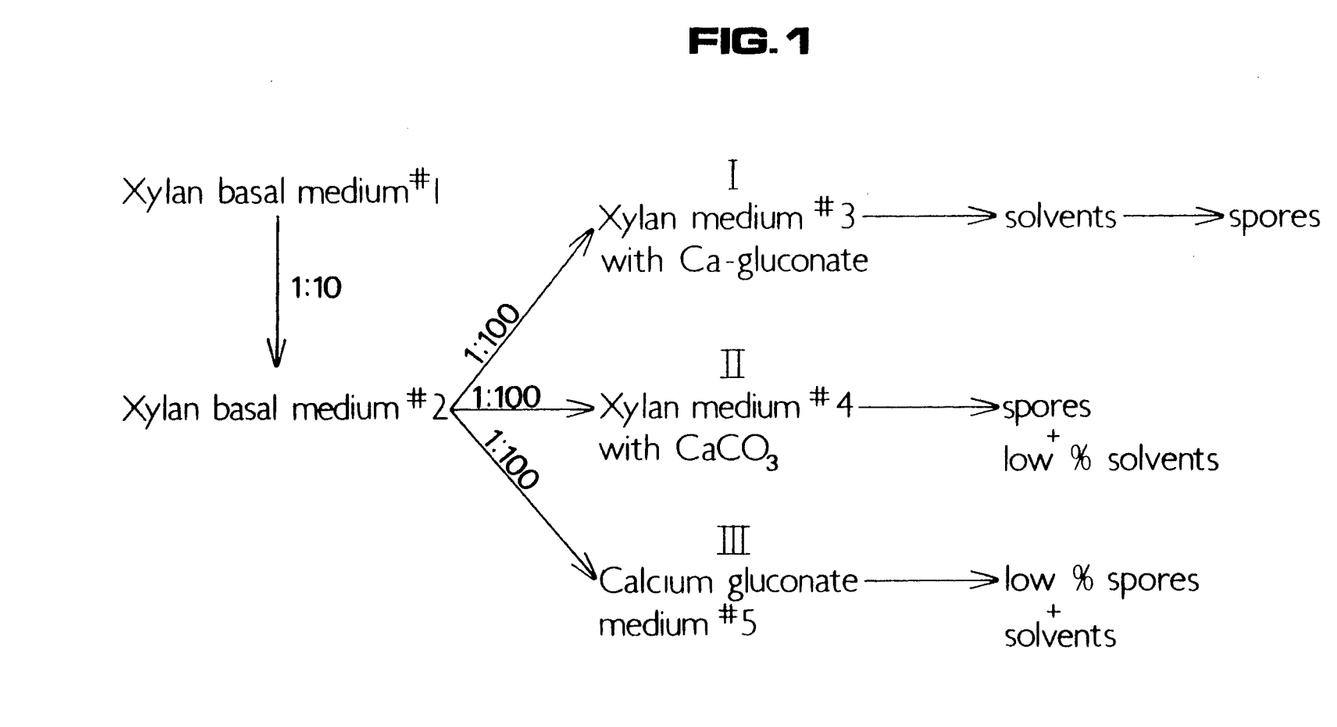
FIG. 1 is a schematic depiction of alternative pathways for production of spores only, spores plus solventogenic cells, or only solventogenic cells.

As is apparent from the schematic representation of FIG. 1, cells which have been subjected to regulated, synchronized growth that induces elongation may be used selectively to carry out separate metabolic processes identified as pathways I, II and III respectively. When the cells are used in a process represented by pathway I, the elongated cells are solventogenic and solvents may be produced for an extended period of time when cell division is arrested. If cell division is inhibited by physical means such as temperature shift and incubation is allowed to proceed, spore formation commences and spores ultimately become the predominant product. If growth is inhibited by antimicrobial agents, even under extended incubation times, solvents remain as the predominant product. When the cells are used in a process represented by pathway II, the result is primarily spore production. When the cells are used in a process as indicated by pathway III, principally solvents are produced.

In accordance with a preferred procedure, a basal growth medium #1 is prepared by supplementing a liquid peptone-yeast extract or other medium of conventional composition with a slowly metabolized carbon source. The preferred medium limits growth of the bacteria to at least about 10% less than the maximum growth rate $K_m$ in an optimum species-specific growth medium. A preferred growth medium in this respect is a pentose material such as xylan. Sufficient xylan should be added to provide about 0.5% of the pentosan on a weight to volume basis.

Xylan, a pentosan compound commonly present in plant cell walls and woody tissue may be obtained by grinding up wheat straw, or any of a number of agricultural, industrial and urban organic waste products. The xylan can be added to the basal medium untreated and in powdered form. Alternatively, the xylan can be hydrolyzed with hot dilute hydrochloric or other acids to yield xylose, a crystalline aldose sugar commonly called wood sugar, having the general formula $C_5H_{10}O_5$. Xylose can also be obtained by coculturing a cellulolytic organism such as *C. thermocellum* along with the *C. thermosaccharolyticum* of the present method on the cellulose basal medium.

A stock culture is prepared by introducing cells of an exponentially growing culture of the genus Clostridium into a suitable broth medium, such as pea broth. Particularly preferred forms of clostridial bacteria are of the species thermosaccharolyicum American Type Culture Collection Strains (ATCC) #7956, National Canner's Association (NCA), #3814. However species which may be used include perfringens ATCC #13124, thermocellum ATCC #27405, thermohydrosulfuricum ATCC #35045, acetobutylicum ATCC #824, thermosulfurigenes ATCC #33743, thermoaceticum Deutsche Sammlung von Mikroorganismen (DSM) #521, thermoautotrophicum DSM #1974, beijerinckii ATCC #25752, and butyricum ATCC #19398.

Synchronization of cell growth may be accomplished by either conventional serial dilution, filtration or centrifugation techniques. Following incubation at the optimum growth temperature and time for a particular clostridial species to reach a cell density of at least about $1 \times 10^6$, about one volume of the stock culture is inoculated for each 10 volumes of the xylan basal medium for incubation as a batch culture, identified as basal medium #1 in FIG. 1.

The basal medium #1 containing the Clostridium batch culture is incubated for a time and a temperature which is specific for the preferred species of Clostridium to multiply two to three times the initial concentration or about 1.0 to 1.5 generations.

A basal growth medium #2 is then prepared which is identical in composition to basal medium #1. About one volume of the Clostridium batch culture in medium #1 is transferred to basal medium #2 for each 10 volumes of the basal medium #2, again for incubation as a batch culture. This culture is similarly maintained at an optimum growth temperature for the species until the culture in medium #2 multiplies two to three times or about 1.0 to 1.5 generations or until the cells reach a concentration of at least about $2-3 \times 10^5$.

A growth medium for use in supporting cell metabolism carried out along one of the metabolic pathways I, or II is prepared by supplementing the xylan basal medium previously described with an organic or inorganic divalent cation source. A growth medium for metabolic pathway III contains a peptone-yeast extract basal medium supplemented with the divalent salt of an organic acid as the sole carbon source. The cation serves to stabilize the cells against death, lysis or aggregation. Preferred divalent cations are magnesium, manganese, iron, zinc, and calcium. Particularly preferred cation sources include organic calcium compounds.

If it is desired to produce both solventogenic cells and spores, metabolic pathway I is used and a preferred stabilization supplement in this respect is calcium gluconate. A growth medium #3 is prepared by supplementing xylan basal medium with at least about 4.3% calcium gluconate on a weight to volume basis (0.1M).

An inoculant of about one volume of the batch culture in basal medium #2 is transferred to growth medium #3 for each 100 volumes of the growth medium. The 1:100 diluted inoculant is incubated as a batch culture for at least about 1 to 12 generations, or 1 to 12 times the "doubling" time or until the cells reach a concentration of about $2 \times 10^{10}$ or 2 to 4,096 times the initial concentration, at which time the cells demonstrate a high degree of synchrony in both cell mass and cell number. About 90% or more of these cells are elongated a minimum of four times and exhibit a modified cell division such that they remain elongated at a critical length of at least three times and preferably four times their vegetative length. Synchronous, solventogenic cells are harvested at the end of this time, with negligible numbers of spores.

Alternatively, the synchronous, solventogenic cells may be subjected to treatment conditions which would inhibit their growth so that the products of their continued metabolic processes may be harvested. DNA replication and cell division may be inhibited by physical means such as increasing or decreasing the temperature of the cells and growth medium from about $+10°$ C. above or $-20°$ C. below the species-specific optimum growth temperature respectively. In other embodiments, growth may be inhibited by application of a sublethal dose of an antimicrobial agent. Particularly preferred antimicrobial agents are chloramphenicol, mitomycin, nalidixic acid, and acridine orange.

Figure 2:
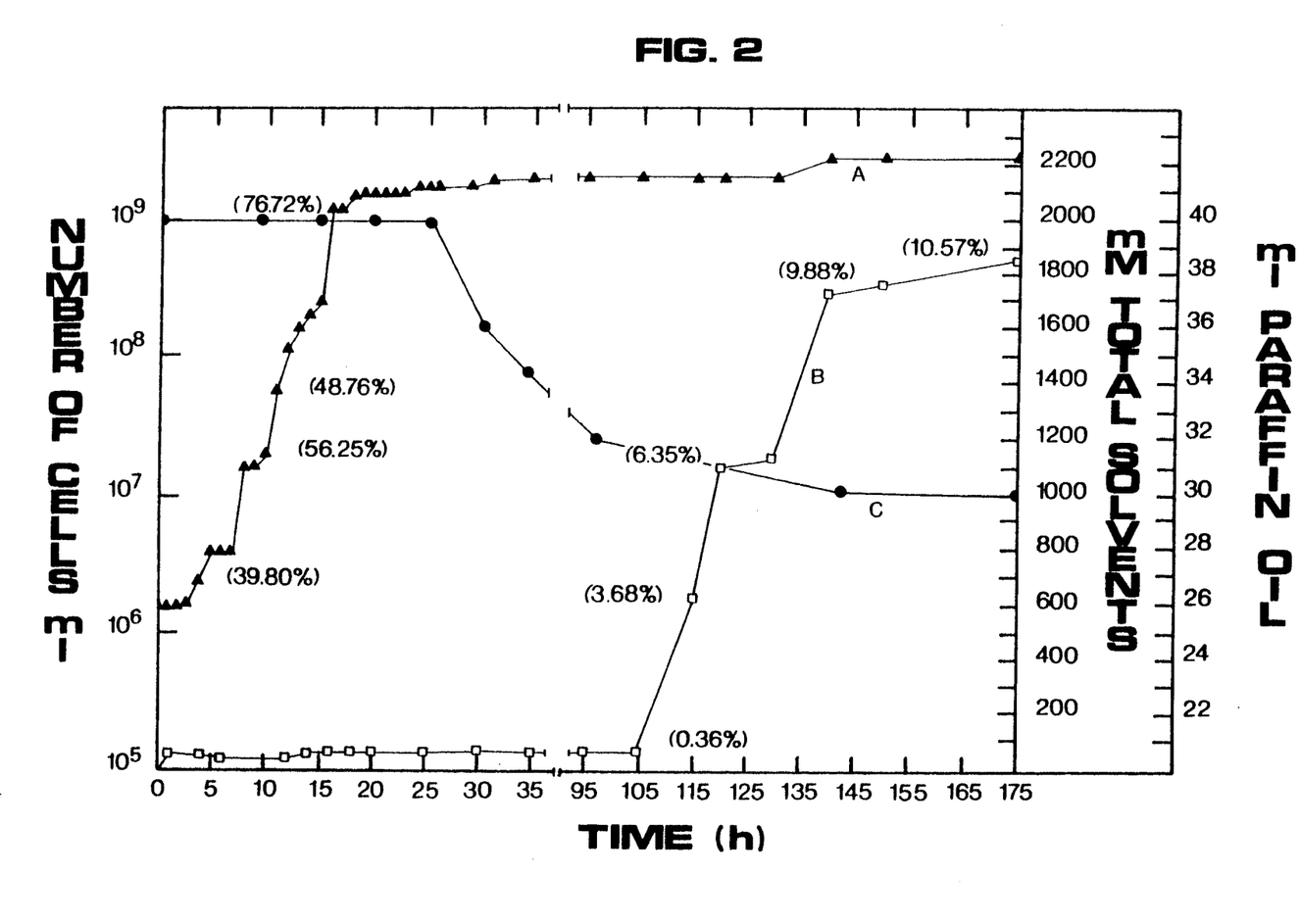
FIG. 2 is a graphic representation of the correlation of synchronous growth, production of solvents, and the utilization of paraffin oil, by a culture incubated in xylan basal medium enriched with calcium gluconate. (Curves A, B and C, respectively).

If the goal is solvent production using metabolic pathway I, division of the elongated solventogenic cells is inhibited and solvent production continues during further incubation with negligible concomitant spore production and utilization of paraffin oil as an additional carbon source. As shown in FIG. 2, inhibition of the specially prepared, synchronized cells causes them to enter a stage of incresing solventogenesis. After a given period of time, which varies depending on the species of bacterium selected, solvent production diminished to a low percentage, indicating continuation of later stages of sporulation.

If incubation is allowed to continue, antibiotics such as polymyxin, bacitracin, carbohydrases such as amylase, proteases, lipases, nucleases, parasporo-like protein crystals, and ultimately, refractile, mature, free spores are produced.

If the desired end product is spores and their related products, then a preferred metabolic pathway is represented by process II of FIG. 1, wherein a preferred divalent cation supplement is calcium carbonate. A growth medium #4 is prepared by supplementing xylan basal medium with about 1.1% calcium carbonate on a weight to volume basis (0.1M).

An inoculant of about one volume of the batch culture in basal medium #2 is transferred to growth medium #4 for each 100 volumes of the growth medium.

The 1:100 diluted inoculant #4 is incubated as a batch culture until the cells again exhibit synchrony in cell mass and number and elongate to at least four times their vegetative length. They exhibit modified cell division such that the daughter cells remain elongated at the critical length. Binary fission of the synchronous cells is inhibited by physical means, such as increasing or decreasing temperature. Continued incubation of this inhibited, synchronized culture results in production of antibiotics, enzymes, parasporo-like crystals, and finally refractile, mature free spores with a low percentage of solvents.

If the desired end product is only solventogenic cells, a preferred metabolic pathway is III of FIG. 1 wherein a medium #5 is prepared for use as a growth medium by supplementing a liquid peptone-yeast extract medium of conventional composition with an organic calcium compound as the sole slowly metabolized carbon source. A preferred organic calcium compound is calcium gluconate present at a level of at least about 4.3% on a weight to volume basis (0.1M).

An inoculant of about one volume of the batch culture in basal medium #2 is transferred to growth medium #5 for each 100 volumes of the growth medium. The 1:100 diluted inoculant #5 is incubated as a batch culture until the cells exhibit synchrony in cell mass and number and elongation to the critical length of about four times their vegetative length with modified cell division. Synchronous, solventogenic cells are harvested at the end of this time, with a low percentage of spores. Where the goal is solvent production using metabolic pathway III, DNA replication and cell division may be inhibited by physical means such as temperature shift, or by use of antimicrobial agents, and the culture is further incubated until solvents are produced, and then continued until solvent production is significantly decreased.

The metabolic products of pathways I, II and III, may be recovered in accordance with various conventional procedures. For example, if the product is a solvent produced at high temperatures, that is to say, temperatures at or above 50° C., recovery may be by vacuum fermentation as described by D. L. Pavia, et al., *Introduction to Organic Laboratory Techniques, A Contemporary Approach*, at 548–552, (W. B. Saunders, 1976), and Cysewski and Wilke, "Rapid Ethanol Fermentation Using Vacuum and Cell Recycle", Vol. XIX Biotechnology and Engineering, 1125–1143, 1977. If the product is a solvent produced at temperatures below 50° C., the product may be recovered by standard distillation processes. Enzymes, such as carbohydrases are extracellular products which are recovered by removing cellular debris by filtration or centrifugution. If further purification of enzymes from crude extract is desired, recovery may be as described by D. I. C. Wang, et al., *Fermentation and Enzyme Technology*, at 238–310, (John Wiley & Sons, 1979). Parasporolike protein crystals and useful toxic proteins are contained within the spores and may be harvested by repeated centrifugation or filtration. The cells are centrifuged or filtered, resuspended, again centrifuged or filtered, resuspended, and again centrifuged or filtered. Pure, dry spores are then recovered. If the product is antibiotics, recovery is by conventional extraction with a solvent such as propanol or butyl acetate as described by Crueger and Crueger in *Biotechnology: A Textbook of Industrial Microbiology*, at 99–103, (Sinauer, Science Tech, 1982).

Growth medium #5 may be substituted in the above described procedures for xylan basal medium #1 and #2. In other respects the procedures remain the same including the final 1:100 dilution into growth medium #5. The dilute inoculant is incubated as a batch culture until the cells exhibit elongation, synchrony and modified cell division as previously described. Synchronous, solventogenic cells are harvested at the end of this time, with negligible numbers of spores.

As another alternative procedure, growth of the synchronous, solventogenic cells may be inhibited to channel the energy of the cells into metabolism rather than cell division and to permit harvesting of the products of their continued metabolic processes. The temperature of the cells and growth medium may be increased to about 10° C. above or decreased to about 20° C. below the species-specific optimum growth temperature respectively, or a sublethal dose of an antimicrobial agent may be administered. The growth-inhibited culture is further incubated and solvents are produced with negligible concomitant spore production. After a given period of time which varies depending on the bacterial species, the percentage of solvents produced varies as, for example from 6% to as high as about 12% and the butanol:ethanol ratio varies as, for example 1:1 to 2:1.

In other embodiments, the step of subculturing in a second basal medium is repeated and the initial dilution into fresh medium is repeated prior to transfer into a third growth medium. The initial dilution into fresh basal medium may be from about 1:2 to 1:100, which may be repeated, and the final dilution may be from about 1:2 to 1:500. Repeated centrifugation or membrane filtration and resuspension may be substituted for serial dilution as a method for synchronization of the cultures. The serial dilution, or separation of cells by filtration or centrifugation, assures that the density level of the bacterial cells present in each succeeding batch subculture is no greater than about one half of the density of the bacterial cells in the immediately preceding culture.

Figure 3:
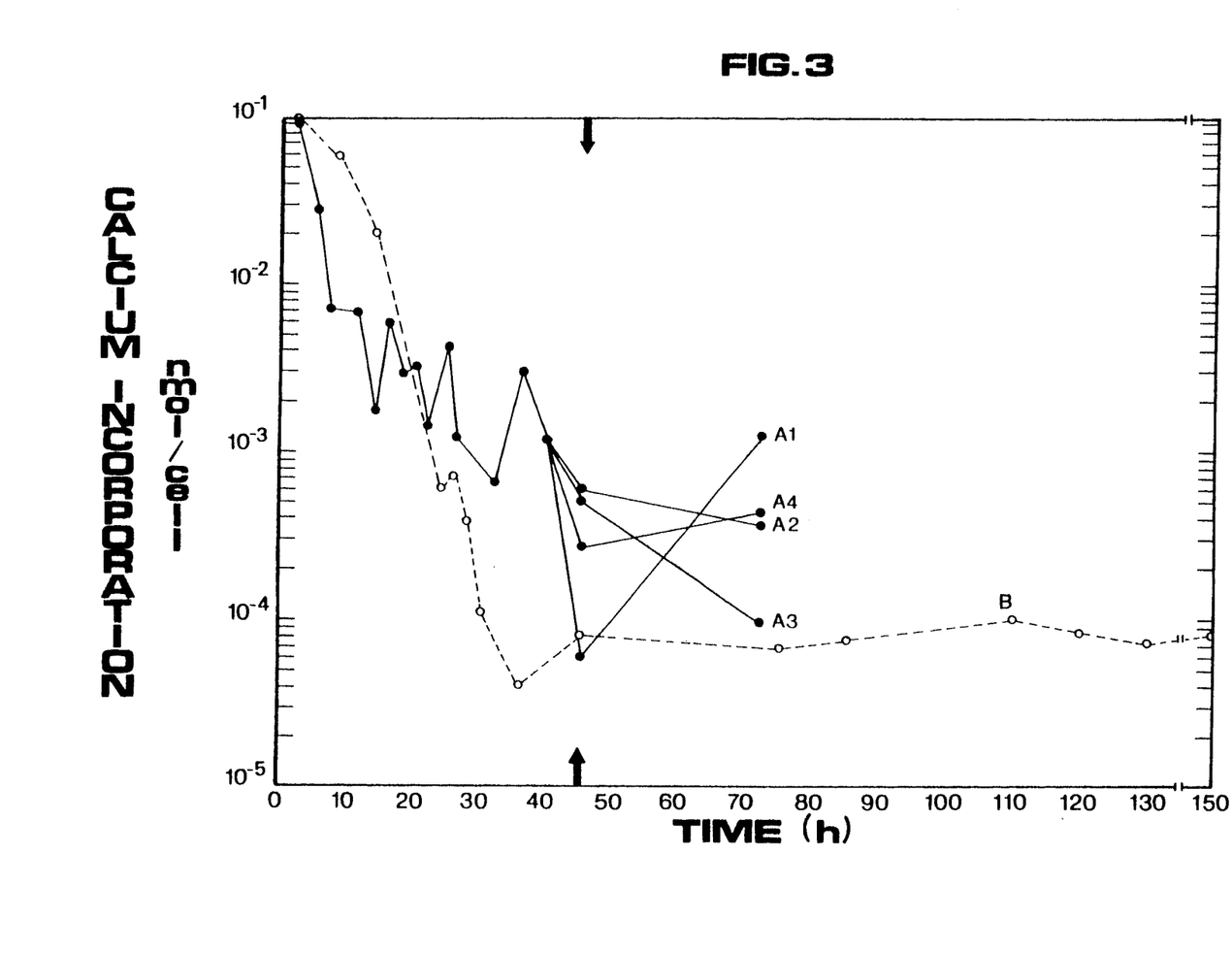
FIG. 3 is a graphic representation of calcium incorporation by an individual cell in the synchronous culture incubated in xylan basal medium enriched with calcium gluconate.
Figure 4:
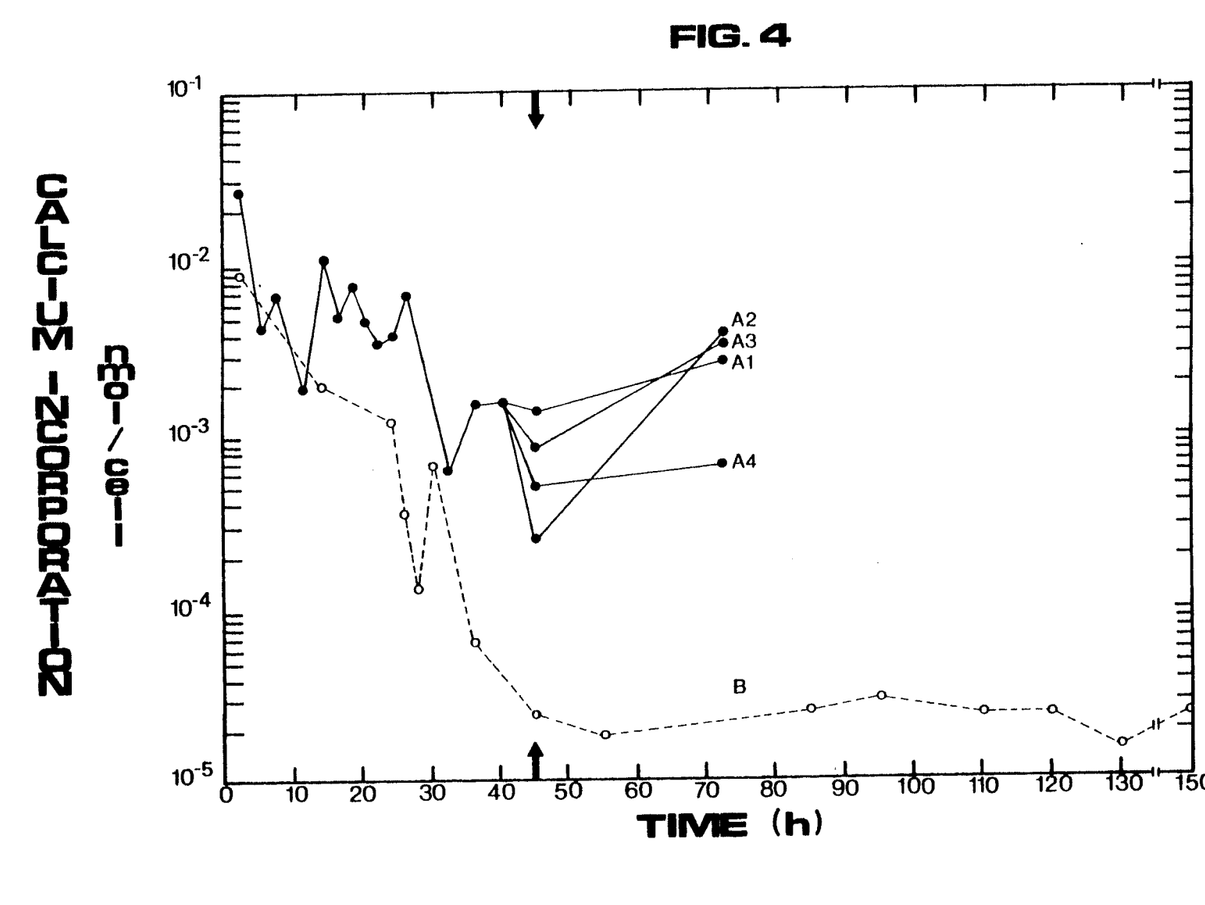
FIG. 4 is a graphic representation of calcium incorporation by an individual cell in the synchronous culture incubated in xylan basal medium enriched with calcium carbonate.
Figure 5:
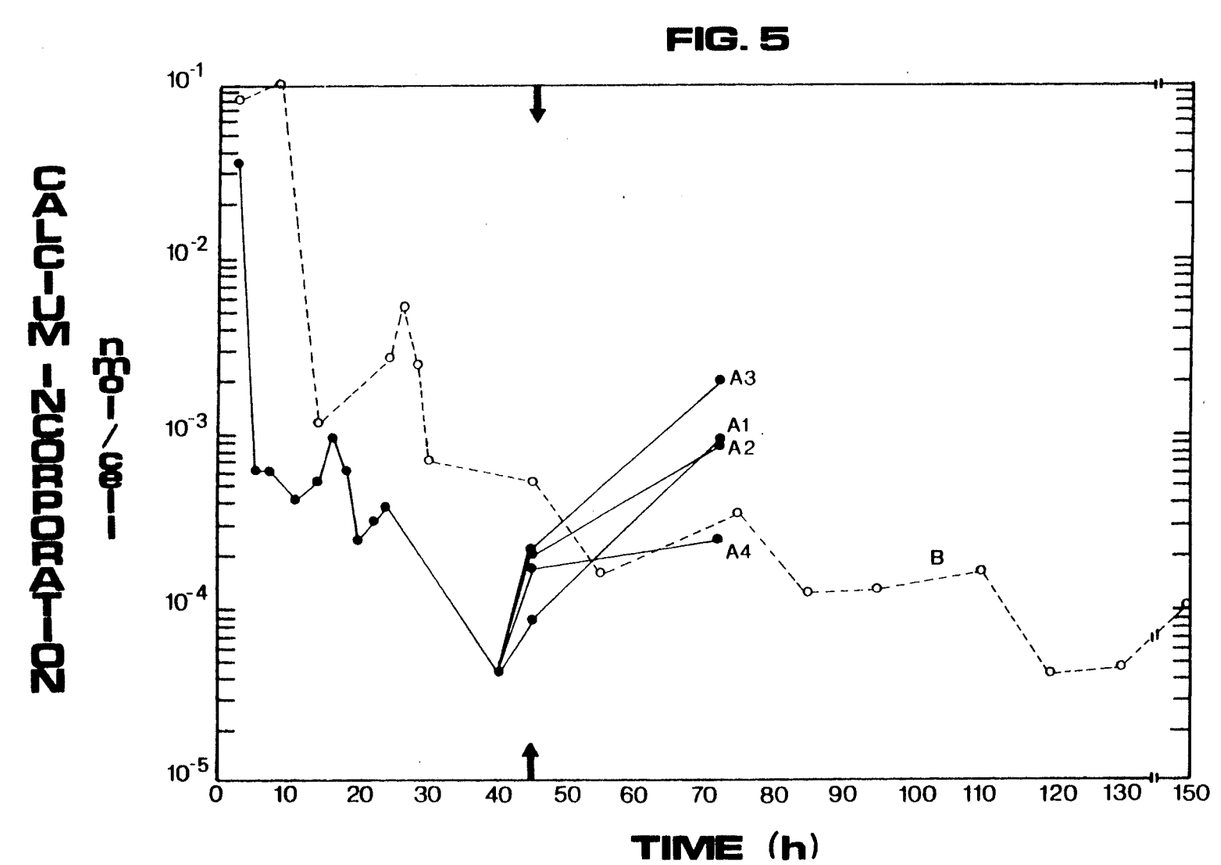
FIG. 5 is a graphic representation of calcium incorporation by an individual cell in the synchronous culture incubated in a calcium gluconate medium.

In all embodiments tested, in order to maintain solventogenesis for extended periods, the elongated, synchronous cells appeared to require a carbon source that is slowly metabolized; normal cell division must be stopped by a temperature shift or the addition of chemical growth inhibitors; and the cells must incorporate calcium. FIGS. 3-5 compare calcium incorporation of individual synchronized *Clostridium thermosaccharolyticum* cells to the calcium incorporation of the typical asynchronous, short, vegetative cells. As illustrated by Curves A1-A4 in each of the Figures, it can be seen that incorporation of calcium stabilized the solventogenic cells and protected them from the high concentrations of solvents that were subsequently produced. Conversely, the Curve B cells of each Figure that were not synchronized prior to the addition of excess calcium, remained as typical, short, vegetative cells, that did not incorporate high concentrations of calcium and were predominantly acidogenic. However, even in these acidogenic cells, when cell division was stopped at 45 hours by shifting to 35° C., the cells elongated, produced solvents, and there was an increase in calcium incorporation.

EXAMPLE I

This example sets forth the preferred procedures for synchronizing the growth of cell number and mass and altering cell division in cultures of wild type *Clostridium thermosaccharolyticum*, (ATCC) #7956.

Pea Broth

Six dried Alaskan seed peas in 10 ml of 2% peptone solution, autoclaved for 15 minutes, immediately overlayed with 2 ml of sterile vaspar.

Stock Cultures

Inoculation of pea broth with an exponentially growing culture of *C. thermosaccharolyticum*, followed by incubation for 8 hours at 56° C. The stock culture was then stored at 4° C. Stock cultures were transferred at 3-6 month intervals. Stock cultures were activated by incubation for 12 hours at 56° C.

Batch Cultures

One ml of activated culture was transferred to 10 ml of fresh basal medium for use as a batch culture.

Basal Medium 0.2% peptone
0.5% yeast extract
0.01% $CaCl_2.2H_2O$
0.1% $(NH_2)_4SO_4$
0.01% $MgSO_4$
0.01% $MnSO_4.H_2O$
0.0005% $ZnSO_4.7H_2O$
0.0005% $CuSO_4.5H_2O$
0.0001% $(NH_4)_6Mo_7O_{24}.4H_2O$
0.00005% $FeSO_4.7H_2O$
0.000002% p-aminobenzoic acid
0.0001% thiamine hydrochloride
0.0000001% biotin
in one liter of water. The thiamine hydrochloride and biotin were filtered, sterilized, and added to the medium after autoclaving. 0.5% (w/v) xylan was added as a carbon source. Media pH was adjusted to 7.0 with 1M NaOH and then sterilized. The medium was preincubated to 56° C. and used within one day.

Procedure

All procedures were performed under anaerobic conditions using the Hungate procedure. A stock culture was activated, transferred to preincubated basal medium containing 0.5% xylan as a carbon source, and incubated at 56° C. for 6 hours, at which time the cell density was approximately $3 \times 10^8$ cells/ml. A 1 ml aliquot of the culture was aseptically transferred to 10 ml of fresh, preincubated xylan basal medium and again allowed to grow as a batch culture at 56° C. After four hours, the culture reached a cell density of approximately $1 \times 10^8$ cells/ml. A 1 ml aliquot of the culture was aseptically transferred to 100 ml of fresh preincubated xylan basal medium which had been supplemented with at least about 4.3% (0.1M) calcium gluconate. The culture was maintained in a serial dilution bottle and overlayed with 40 ml of sterile paraffin oil to ensure maintenance of anaerobic conditions. The culture was incubated in a rotary water bath shaker at 56° C. and 150 rpm. After 45 hours, the culture reached a cell density of approximately $2 \times 10^9$ cells/ml.

These solventogenic cells were harvested by centrifugation at $22,000 \times g$ for 30 minutes, resuspended in sterile distilled water, centrifuged at $22,000 \times g$ for 30 minutes, resuspended in sterile distilled water, centrifuged at 22,000× g for 30 minutes, at which point the cells were ready for immobilization and storage at 4° C.

The cells were differentially counted under a microscope using a Petroff Hausser counting chamber to determine the total number of cells, length of individual cells, number of sporangia, and number of refractile spores. An Olympus phase contrast microscope with a magnification of 400× was used. The morphology was confirmed at 1,000×.

The culture supernatant fluid was analyzed by gas-liquid chromatography (GLC) using a Hewlett-Packard GLC, Model 5700, equipped with a flame ionization detector and strip-chart recorder. Primary metabolites were separated on a stainless steel column (0.31 cm by 1.82 m) packed with 100/120 Chromosorb W AW coated with 10% SP-1000/1% $H_3PO_4$ (Supelco, Inc.). The column was conditioned for 48 hours at 200° C. For analysis the injection port temperature was 200° C. and the detector temperature was 250° C. Prepurified nitrogen was used as the carrier gas with a flow rate of 40 ml/min. Hydrogen and compressed air flow rates were 30 and 300 ml/min, respectively. The electrometer range was set at $10^{-11}$ A/mv with an attenuation of 16 and a range of 10. The oven temperature was held at 80° C. for 2 minutes after injection of the 10 microliter sample, then programmed to 170° C. at a range of 8° C./min, followed by a 2 minute hold period. Metabolite percentages were calculated from the area of standard reference peaks and converted to millimolar concentrations.

Samples obtained for counting and GLC analysis were subsequently centrifuged at 2200× g for 30 minutes to separate the cells from the culture medium. The cells were resuspended in sterile distilled water and the procedure repeated three times, following which the pellet was resuspended in 5 ml of sterile distilled water and sonicated to 90% disruption, as confirmed by phase-contrast microscopy. A model 400 Dionex ion chromatograph equipped with a Hewlett-Packard 9000 computer and autosampler was used for ion chromatographic analysis. Cations were separated on a CS-1 column. The eluent for sodium, ammonium, and potassium was 8 mM HCl plus 1 mM 2,3-diaminopropionic acid at 2.0 ml/min. The eluent for magnesium, manganese, and calcium was 48 mM HCl plus 8 mM 2,3-diaminopropionic acid at a flow rate of 0.8 ml min$^{-1}$. Anions were separated on an AS4A column using an eluent of 1.92 mM sodium carbonate plus 2.4 mM sodium bicarbonate at 2.0 ml/min.

Results

Cultures synchronized by repeated transfer in xylan medium within 6 hours and subsequently grown for 45 hours in the presence of xylan enriched with excess calcium gluconate demonstrated a high degree of synchrony both in cell mass and cell number. Differential count of the cells revealed 69.3% synchrony in cell mass and 76.7% synchrony in cell number. More than 90% of these synchronous, solventogenic cells elongated a minimum of four times and exhibited a modified cell division such that they remained elongated at a critical length of at least four times vegetative length. The number of refractile spores was negligible.

EXAMPLE II

The procedure of Example I was repeated except that the first incubation of a 1:10 dilution of the stock culture was followed by a second incubation of a 1:10 dilution of the culture in fresh, preincubated xylan basal medium. This dilution was again allowed to grow as a batch culture at 56° C. After 4 hours, the culture reached a cell density of approximately $1 \times 10^8$, and the remainder of the procedure of Example I was completed. More than 90% of these synchronous cells elongated a minimum of four times and exhibited a modified cell division such that they remained elongated at a critical length of at least four times vegetative length. The number of refractile spores was negligible.

EXAMPLE III

The procedure of Example I was repeated except that after 45 hours the temperature was lowered to 35° C. by dipping the culture in an ice bath and transferring it to a rotary incubator at 35° C. The culture was incubated for an additonal 135 hours (180 hours total incubation time) at 35° C. After 180 hours the culture reached a cell density of approximately $2 \times 10^9$ cells/ml. Cells prepared in this manner produced 10.6% solvents with a butanol:ethanol ratio of 2:1.

Correlation of synchrony in cell number and corresponding concentration of solvents is shown in FIG. 5. Curve A shows the total cell count, with the degree of synchrony shown parenthetically as a percentage. Curve B shows the absolute concentration of solvents produced, with alcohol shown parenthetically on a volume/volume basis. The total millimolar solvent concentration is equal to the sum of the concentrations of the individual solvents: acetone, butanol, ethanol, isopropanol, and methanol.

Although solvents were produced from the beginning of the fermentation, the total millimolar concentrations, shown in Curve B, were relatively low during the synchronous growth period shown in Curve A. When the temperature was shifted to 35° C. after 45 hours of incubation, the arrested, elongated cells entered a stage of increasing solventogenesis such that at 115 hours the total concentration was 3.6%, at 130 hours the concentration increased to 6.3%, and at 145 hours the concentration further increased to 9.8%. The highest concentration of solvents, 10.6%, was observed at 175 hours.

EXAMPLE IV

The procedure of Example III was repeated except that following the reduction in temperature the culture was incubated for an additional 155 hours (200 hours total incubation time) at 35° C. After 200 hours the culture reached a cell density of approximately $2 \times 10^9$ cells/ml. Cells prepared in this manner produced 6.5% solvents with a butanol:ethanol ratio of 1:1.

EXAMPLE V

The procedure of Example III was repeated except that following the reduction in temperature the culture was incubated for an additional 200 hours (245 hours total incubation time) at 35° C. After 245 hours the culture reached a cell density of approximately $2 \times 10^9$ cells/ml. Cells prepared in this manner produced significant amounts of antibiotics, such as polymyxin, bacitracin, carbohydrases such as amylase, proteases, lipases, nucleases; parasporo-like protein crystals, and refractile, mature, free spores.

EXAMPLE VI

The procedure of Example I was repeated except that after 45 hours the temperature was increased to 70° C. by transferring the culture to a rotary incubator at 70°

C. The culture was incubated an additional 135 hours (180 hours total incubation time) at 70° C. After 180 hours the culture reached a cell density of approximately $2 \times 10^9$ cells/ml. Cells prepared in this manner produced 10.6% solvents with a butanol:ethanol ratio of 2:1.

EXAMPLE VII

The procedure of Example VI was repeated except that after increasing the temperature to 70° C. the culture was incubated an additional 155 hours (200 hours total incubation time) at 70° C. After 200 hours the culture reached a cell density of approximately $2 \times 10^9$ cells/ml. Cells prepared in this manner produced 6.5% solvents with a butanol:ethanol ratio of 1:1.

EXAMPLE VIII

The procedure of Example VI was repeated except that after shifting the temperature to 70° C. the culture was incubated an additional 200 hours (245 hours total incubation time) at 70° C. After 245 hours the culture reached a cell density of approximately $2 \times 10^9$ cells/ml. Cells prepared in this manner produced antibiotics, carbohydrases, parasporo-like protein crystals, and refractile, mature, free spores.

EXAMPLE IX

The procedure of Example I was repeated except that after 45 hours chloramphenicol was added to give a 20 micromolar final concentration in order to prevent further cell division. The culture was incubated for an additional 27 hours (72 hours total incubation time). After 27 hours the culture reached a cell density of approximately $2 \times 10^9$ cells/ml. Cells prepared in this manner produced 10.6% solvents with a butanol:ethanol ratio of 2:1

EXAMPLE X

The procedure of Example IX was repeated except that after addition of chloramphenicol the culture was incubated an additional 42 hours (87 hours total incubation time). After 87 hours the culture reached a cell density of approximately $2 \times 10^9$ cells/ml. Cells prepared in this manner produced 6.5% solvents with a butanol:ethanol ratio of 1:1.

Calcium incorporation by an individual cell in the synchronous culture incubated in xylan basal medium enriched with calcium gluconate is shown in FIG. 3. The highest solvent production correlated with the highest calcium incorporation as shown in Curves A1-A4. Cell division was stopped at 45 hours by addition of chloramphenicol in Curve A1, nalidixic acid in Curve A2, mitomycin in Curve A3, and acridine orange in Curve A4. The cells treated with nalidixic acid of Curve A2 produced 7.1% solvents at 72 hours, which correlated with the highest incorporation of calcium, 3,162 nanomoles. When acridine orange was added to the synchronized cells in the same medium, shown in Curve A4, the solvent concentration reached 8.1% with calcium incorporation of 1,163 nanomoles. Curve B represents the calcium incorporation by an individual cell in an asynchronous culture incubated in the same medium.

EXAMPLE XI

The procedure of Example I was repeated except that a sporulation medium of xylan with 1.1% (0.1M) calcium carbonate was used. After 45 hours the cells exhibited a high degree of synchrony both in mass and number. Differential count of the cells revealed 48.8% synchrony in cell mass and 56.3% synchrony in cell number. More than 90% of these synchronous, solventogenic cells elongated a minimum of four times and exhibited a modified cell division such that they remained elongated at a critical length of at least four times vegetative length. The number of refractile, mature free spores was negligible.

EXAMPLE XII

The procedure of Example XI was repeated except that after 45 hours, the temperature was lowered to 35° C. by dipping the culture in an ice bath and transferring it to a rotary incubator at 35° C. The culture was incubated for an additional 200 hours (245 hours total incubation time) at 35° C. After 245 hours the culture reached a density of approximately $2 \times 10^9$ cells/ml. Cells prepared in this manner produced antibiotics, carbohydrases, parasporo-like protein crystals, and refractile, mature, free spores.

EXAMPLE XIII

The procedure of Example XII was repeated except that after 45 hours, the temperature was increased to 70° C. by transferring the culture to a rotary incubator at 70° C. The culture was incubated for an additional 200 hours (245 hours total incubation time) at 70° C. After 245 hours, the culture reached a density of approximately $2 \times 10^9$ cells/ml. Cells prepared in this manner produced antibiotics, carbohydrases, parasporo-like protein crystals, and refractile, mature, free spores.

EXAMPLE XIV

The procedure of Example XI was repeated except that after 45 hours nalidixic acid was added to give a 20 micromolar final concentration in order to prevent further cell division. The culture was incubated for an additional 27 hours (72 hours total incubation time). After 27 hours, the culture reached a cell density of approximately $2 \times 10^9$ cells/ml. Cells prepared in this manner produce negligible solvents and may produce antibiotics, carbohydrases, parasporo-like protein crystals, and refractile, mature, free spores.

Calcium incorporation by an individual cell in the synchronous culture incubated in xylan basal medium enriched with calcium carbonate is shown in FIG. 4. Although these cells did not produce high concentrations of solvents, the highest solvent production (0.2-0.4%) correlated with the highest calcium incorporation as shown in Curves A1-A4. Cell division was stopped at 45 hours by addition of chloramphenicol in Curve A1, nalidixic acid in Curve A2, mitomycin in Curve A3, and acridine orange in Curve A4. The synchronous cells inhibited with nalidixic acid of Curve A2 incorporated 12,492 nanomoles of calcium at 72 hours and 40-50% of the cells showed signs of terminal swelling indicative of Stage IV to V of sporulation. In contrast, synchronous cells in the same medium inhibited with acridine orange of Curve A4 incorporated 754 nanomoles of calcium and produced 0.4% solvents. Curve B represents the calcium incorporation by an individual cell in the asynchronous culture incubated in the same medium.

EXAMPLE XV

The procedure of Example I was repeated except that a sporulation medium with at least 4.3% calcium gluconate as the sole carbon source was used. After 45 hours the culture reached a density of approximately $2 \times 10^9$ cells/ml. Cells prepared in this manner were highly elongated and solventogenic. Refractile, mature, free spores or refractile sporangia were not produced in significant amounts.

EXAMPLE XVI

The procedure of Example XV was repeated except that after 45 hours the temperature was lowered to 35° C. by dipping the culture in an ice bath and transferring it to a rotary incubator at 35° C. The culture was incubated for 135 hours (180 hours total incubation time) at 35° C. After 180 hours the culture reached a density of approximately $2 \times 10^9$ cells/ml. Cells prepared in this manner produced 10.6% solvents with a butanol:ethanol ratio of 2:1.

EXAMPLE XVII

The procedure of Example XV was repeated except that after temperature reduction the cells are incubated an additional 155 hours (195 hours total incubation time). After 195 hours the culture reached a density of approximately $2 \times 10^9$ cells/ml. Cells prepared in this manner produced 6.5% solvents with a butanol:ethanol ratio of 1:1.

EXAMPLE XVIII

The procedure of Example XV was repeated except that after 45 hours the temperature was increased to 70° C. by transferring the culture to a rotary incubator at 70° C. The culture was incubated an additional 135 hours (180 hours total incubation time) at 35° C. After 180 hours the culture reached a density of approximately $2 \times 10^9$ cell/ml. Cells prepared in this manner produced 10.6% solvents with a butanol:ethanol ratio of 2:1.

EXAMPLE XIX

The procedure of Example XVIII was repeated except that after increasing the temperature the culture was incubated an additional 155 hours (195 hours total incubation time) at 70° C. After 195 hours the culture reached a density of approximately $2 \times 10^9$ cells/ml. Cells prepared in this manner produced 6.5% solvents with a butanol:ethanol ratio of 1:1.

EXAMPLE XX

The procedure of Example XV was repeated except that after 45 hours chloramphenicol was added to give a 20 micromolar final concentration in order to prevent further cell division. The culture was incubated for an additional 27 hours (72 hours total incubation time). After 27 hours the culture reached a cell density of approximately $2 \times 10^9$ cells/ml. Cells prepared in this manner produced 10.6% solvents with a butanol:ethanol ratio of 2:1.

EXAMPLE XXI

The procedure of Example XV was repeated except that after the addition of chloramphenicol the culture was incubated an additional 42 hours (87 hours total incubation time). After 87 hours the culture reached a cell density of approximately $2 \times 10^9$ cells/ml. Cells prepared in this manner produced 6.5% solvents with a butanol:ethanol ratio of 1:1.

Calcium incorporation by an individual cell in the synchronous culture incubated in calcium gluconate medium is shown in FIG. 5. The correlation between the peak in solventogenesis and calcium incorporation is shown in Curves A1–A4. Cell division was stopped at 26 hours by addition of chloramphenicol in Curve A1, nalidixic acid in Curve A2, mitomycin in Curve A3, and acridine orange in Curve A4. The synchronous cells treated with nalidixic acid of Curve A2 produced 9.1% solvents at 72 hours, which correlated with the incorporation of 1,940 nanomoles of calcium. Curve B represents the calcium incorporation by an individual cell in the asynchronous culture incubated in the same medium.

EXAMPLE XXII

The procedure of Example I was repeated except that the basal medium contained at least 4.3% calcium gluconate was used as the sole carbon source. After 26 hours the culture reached a density of approximately $2 \times 10^9$ cells/ml. Cells prepared in this manner were highly elongated and solventogenic. Refractile, mature, free spores or refractile sporangia were not produced in significant amounts.

EXAMPLE XXIII

The procedure of Example XII was repeated except that after 26 hours the temperature was lowered to 35° C. by dipping the culture in an ice bath and transferring it to a rotary incubator at 35° C. The culture was incubated for 135 hours (180 hours total incubation time) at 35° C. After 180 hours the culture reached a density of approximately $2 \times 10^9$ cells/ml. Cells prepared in this manner produced 10.6% solvents with a butanol:ethanol ratio of 2:1.

EXAMPLE XXIV

The procedure of Example XXII was repeated except that after temperature reduction the cells are incubated an additional 155 hours (195 hours total incubation time). After 195 hours the culture reached a density of approximately $2 \times 10^9$ cells/ml. Cells prepared in this manner produced 6.5% solvents with a butanol:ethanol ratio of 1:1.

EXAMPLE XXV

The procedure of Example XXII was repeated except that after 26 hours the temperature was increased to 70° C. by transferring the culture to a rotary incubator at 70° C. The culture was incubated an additional 135 hours (180 hours total incubation time) at 35° C. After 180 hours the culture reached a density of approximately $2 \times 10^9$ cells/ml. Cells prepared in this manner produced 10.6% solvents with a butanol:ethanol ratio of 2:1.

EXAMPLE XXVI

The procedure of Example XXV was repeated except that after increasing the temperature the culture was incubated an additional 155 hours (195 hours total incubation time) at 70° C. After 195 hours the culture reached a density of approximately $2 \times 10^9$ cells/ml. Cells prepared in this manner produced 6.5% solvents with a butanol:ethanol ratio of 1:1.

EXAMPLE XXVII

The procedure of Example XXII was repeated except that after 26 hours chloramphenicol was added to give a 20 micromolar final concentration in order to prevent further cell division. The culture was incubated for an additional 27 hours (72 hours total incubation time). After 27 hours the culture reached a cell density of approximately $2 \times 10^9$ cells/ml. Cells prepared in this manner produced 10.6% solvents with a butanol:ethanol ratio of 2:1.

EXAMPLE XXVIII

The procedure of Example XXII was repeated except that after the addition of chloramphenicol the culture was incubated an additional 42 hours (87 hours total incubation time). After 87 hours the culture reached a cell density of approximately $2 \times 10^9$ cells/ml. Cells prepared in this manner produced 6.5% solvents with a butanol:ethanol ratio of 1:1.

The use of an oleaginous material as an overlay for the growth medium during cell multiplication serves the dual function of maintaining an anaerobic environment for growth of the cells and at the same time provides a secondary carbon source. A saturated hydrocarbon such as paraffin oil is the preferred oleaginous agent, primarily because of its availability at a reasonable cost. Furthermore, the use of paraffin oil as an overlay for the growth medium allows a standard vessel to be used for fermentation thus avoiding the necessity of employing expensive fermentation equipment which usually incorporates cooling apparatus, aeration and agitation means. In the present process, slow mechanical mixing of the growth medium is adequate under conditions such that the agitation does not interfere with the oxygen-excluding, coherent characteristics of the oleaginous layer. An open top concrete, metal or wood vessel is suitable in this respect, thus permitting the utilization of existing structures.

In like manner, in view of the fact that the only external energy required is that necessary to increase the temperature of the growth medium to a required level, e.g., about 56° C. in the case of C. thermosaccharolyticum, thermal energy obtained from solar power will in many instances be adequate, particularly if the growth medium is introduced into a metal walled vessel exposed to the sun. In the case where the carbon source is the spent liquor from a pulp mill, that liquor is generally available out of the plant at a temperature of at least about 90° C. and therefore need only to be allowed to cool to the desired level before being used in the fermentation processes described herein.

We claim:

1. A process for producing bacterial cells useful in selective production of spores and a metabolic end product selected from the group consisting of solvents, enzymes, antibiotics and useful toxic proteins, and comprising the steps of:

providing an initial stock culture containing a carbon source in a growth medium, and at least about $1 \times 10^6$ cells per milliliter of bacteria of the genus Clostridium, said bacterial cells, when treated to inhibit division, being genetically capable of metabolizing a carbon source to produce spores or a metabolic end product selected from the group consisting of said solvents, enzymes, antibiotics and proteins;

providing a quantity of a divalent cation source;

inducing elongation of said bacterial cells under conditions to produce modified cells of a critical length of at least about $3 \times$ while synchronizing the growth in the number of said cells and their effective mass by (a) preparing from the initial stock culture another batch subculture which contains a quantity of a slowly metabolizable carbon source other than glucose in a growth medium by adding to the other batch subculture bacterial cells obtained from the initial stock culture and present at a density level no greater than about one half of the density of the bacterial cells present in the initial stock culture;

(b) incubating said other batch subculture within a time to cause the cells therein to multiply for only about one to one and one half generations in said batch subculture while maintaining the growth medium at a temperature within a range of about $-20°$ C. to $+10°$ C. of the species-specific optimum growth temperature, said growth medium being devoid of an amount of cellular metabolites that would be sufficient to substantially interfere with synchronous growth of said cells, (c) preparing from an immediately preceding batch subculture a final batch subculture which contains a quantity of a slowly metabolizable carbon source other than glucose in a growth medium by adding to said final batch subculture bacterial cells obtained from the immediately preceding batch subculture and present at a density level no greater than about one half of the density of the bacterial cells present in said immediately preceding batch subculture;

(d) incubating said final batch subculture for a time to cause the cells therein to multiply while maintaining the growth medium at a temperature within the range of step (b), said growth medium being devoid of an amount of cellular metabolites that would be sufficient to substantially interfere with synchronous growth of said cells, and (e) carrying out at least incubation step (d) in the presence of at least about 0.01M of said divalent cation and which is sufficient to cause cellular incorporation of an amount of said divalent cation into said elongated cells during step (d) to stabilize the cells against death, lysis and aggregation and cause modified cell division in a manner such that, as each cell divides into two cells, the resulting divided cells remain elongated to at least said $3 \times$ length, said slowly metabolizable carbon source being selected in each instance to cause the bacteria to grow in the selected growth medium at a rate of about 10%–90% less than the maximum growth rate $K_m$ for the bacteria in an optimum growth medium; and thereafter selectively subjecting the cells resulting from step (d) to treatment conditions which thereafter inhibit cell division and cause the cells to primarily produce either spores or at least one of said metabolic end products.

2. The process as set forth in claim 1, wherein step (e) includes providing said divalent cation at a concentration of at least about 0.01M to about 0.2M.

3. The process as set forth in claim 1, wherein the step of subjecting the cells resulting from step (d) to treatment conditions which inhibit cell division includes adding an antimicrobial agent selected from the group consisting of chloramphenicol, mitomycin, nalidixic acid, and acridine orange.

4. The process as set forth in claim 1, wherein the step of subjecting the cells from step (d) to treatment conditions which inhibit cell division includes reducing the temperature of said cells below the range specified in step (b).

5. The process as set forth in claim 1, wherein the step of subjecting the cells resulting from step (d) to treatment conditions which inhibit cell division includes increasing the temperature of said cells above the range specified in step (b).

6. The process as set forth in claim 1, wherein the growth medium includes a substantial proportion of a pentose polymer.

7. The process as set forth in claim 6, wherein the growth medium includes a substantial proportion of a slowly metabolizable carbon source selected from the group consisting of amygdalin, arabinose, cellobiose, galactose, glycogen, melibiose, α-methylglucoside, β-methyl glucoside, raffinose, salicin, starch, trehalose, xylan, Ca-acetate, Ca-butyrate, Ca-citrate, Ca-formate, Ca-gluconate, and Ca-lactate.

8. The process as set forth in claim 1, wherein the growth medium is a medium containing a substantial proportion of a starting material selected from the group consisting of wheat straw, rice straw, rice hulls, corn stalks and corn cobs, saw dust, wood chips, cellulose and hemicellulosic residues.

9. The process as set forth in claim 1, wherein said divalent cation source contains cations selected from the group consisting of magnesium, manganese, iron, zinc and calcium.

10. The process as set forth in claim 1, wherein said divalent cation source contains an organic calcium compound selected from the group consisting of Ca-gluconate, Ca-lactate, Ca-acetate, Ca-butyrate, Ca-formate, Ca-carbonate and Ca-sulfate.

11. A spore or metabolic product made in accordance with the process of claim 1.

12. A spore or metabolic end product in accordance with the process of claim 1.

13. The process as set forth in claim 10, wherein said oleaginous material is a paraffin oil.

14. The process as set forth in claim 10, wherein is included the step of mechanically agitating the growth medium without interfering with the oxygen excluding integrity of the oleaginous layer thereover during multiplication of the cells in the growth medium.

15. The process as set forth in claim 1, wherein said modified cell elongation and synchronization of growth in the number of said cells and their effective mass is accomplished by:
carrying out at least one additional subculture and incubation step between steps (c) and (d) of claim 1 wherein in each instance a batch subculture is prepared which contains a quantity of said slowly metabolizable carbon source in a growth medium and bacterial cells obtained from the immediately preceding batch subculture at a density level no greater than about one half of the density of the bacterial cells present in the immediately preceding batch subculture, and the batch subculture thus prepared incubated for a time to cause the cells therein to multiply only about one to one and one half generations.

16. The process as set forth in claim 1, wherein each batch subculture and the final subculture are prepared by removing an aliquot of the growth medium containing said cells from the initial stock culture and a preceding batch subculture respectively and diluting each aliquot from about 1:2 to about 1:100 with a fresh quantity of a growth medium which contains a quantity of said slowly metabolizable carbon source.

17. The process as set forth in claim 1, wherein each batch subculture is prepared by removing an aliquot of the growth medium containing said cells from the initial stock culture and a preceding batch subculture respectively and diluting each aliquot from about 1:2 to about 1:500 with a fresh quantity of a growth medium which contains a quantity of said slowly metabolizable carbon source.

18. The process as set forth in claim 1, wherein the step of adding said cells to corresponding subcultures includes the step of separating the cells from said stock culture and a preceding subculture respectively by centrifugation.

19. The process as set forth in claim 1, wherein the step of adding said cells to corresponding subcultures includes the step of separating the cells from said stock culture and a preceding subculture respectively by membrane filtration.

20. The process as set forth in claim 1, wherein said subculturing and incubation steps are all carried out under anaerobic conditions and including the step of maintaining a layer of an oleaginous material over the growth medium to serve as a secondary carbon source.

21. The process as set forth in claim 1, wherein said slowly metabolizable carbon source in steps (a) and (c) is the divalent cation source.

22. The process as set forth in claim 21, wherein said source is calcium gluconate.

* * * * *